(12) United States Patent
Niezgoda et al.

(10) Patent No.: US 12,605,530 B1
(45) Date of Patent: Apr. 21, 2026

(54) SENSOR ENABLED THERAPEUTIC WOUND AND TISSUE MONITOR

(71) Applicants: Jeffrey A. Niezgoda, Greendale, WI (US); Eric J. Roberts, Greendale, WI (US); Jonathan A. Niezgoda, Greendale, WI (US)

(72) Inventors: Jeffrey A. Niezgoda, Greendale, WI (US); Eric J. Roberts, Greendale, WI (US); Jonathan A. Niezgoda, Greendale, WI (US)

( * ) Notice: Subject to any disclaimer, the term of this patent is extended or adjusted under 35 U.S.C. 154(b) by 299 days.

(21) Appl. No.: 18/195,219

(22) Filed: May 9, 2023

Related U.S. Application Data

(60) Provisional application No. 63/339,567, filed on May 9, 2022.

(51) Int. Cl.
  *A61F 13/00* (2024.01)
  *A61F 13/05* (2024.01)
  (Continued)

(52) U.S. Cl.
  CPC ....... *A61M 35/30* (2019.05); *A61F 13/00063* (2013.01); *A61F 13/05* (2024.01);
  (Continued)

(58) Field of Classification Search
  CPC ...... A61F 2007/0052; A61F 2007/0071; A61F 2007/0261; A61F 7/007; A61F 2/1613; A61F 2/1627; A61F 9/061; A61F 13/05;

A61F 2/06; A61F 2/86; A61F 2/91; A61F 11/085; A61F 11/10; A61F 11/145; A61F 13/00; A61F 13/00051; A61F 2013/00536;
(Continued)

(56) References Cited

U.S. PATENT DOCUMENTS 4,962,769 A    10/1990  Garcia
5,356,372 A    10/1994  Donovan et al.
(Continued)

OTHER PUBLICATIONS

Edsberg LE, et al., Revised National Pressure Ulcer Advisory Panel Pressure Injury Staging System: Revised Pressure Injury Staging System. J Wound Ostomy Continence Nurs. 2016;43(6):585-597.
(Continued)

*Primary Examiner* — Kim M Lewis
(74) *Attorney, Agent, or Firm* — Nyemaster Goode P.C.

(57) ABSTRACT

A therapeutic device used for monitoring a wound includes an external layer impermeable to gas and moisture with a periphery that adheres to a user's skin about the wound and an internal layer with a periphery adhered to the external layer creating a gaseous reservoir between the external and internal layers. The internal layer is semipermeable to allow gas to diffuse from the gaseous reservoir toward the wound, and to allow moisture to be absorbed from the wound. A spacer layer separates the external and internal layers and absorbs fluid from the wound. A bendable, flexible and stretchable, film-based circuit board is located on the internal layer and includes a processor, at least one sensor, and a wireless transceiver. A perforated inner wound layer is positioned below the circuit board and includes openings configured to allow the at least one sensor to be in communication with the wound.

25 Claims, 7 Drawing Sheets

(51) Int. Cl.
  *A61M 1/00*          (2006.01)
  *A61M 35/00*          (2006.01)
(52) U.S. Cl.
  CPC ... *A61M 35/10* (2019.05); *A61F 2013/00906*
      (2013.01); *A61M 2202/0208* (2013.01); *A61M*
        *2205/3303* (2013.01); *A61M 2205/3313*
                  (2013.01)
(58) Field of Classification Search
  CPC .......... A61F 13/0226; A61F 2013/0054; A61F
            13/00055; A61F 13/00063; A61F
        13/0213; A61F 13/0276; A61F 13/0289;
        A61F 2/50; A61F 2/76; A61F 2002/5001;
        A61F 2002/5061; A61F 2002/5063; A61F
            2002/7635; A61F 2002/7665; A61F
        2002/767; A61F 2013/0011; A61F 5/56;
        A61F 13/01008; A61F 13/01029; A61F
        13/01034; A61F 13/0203; A61F 13/0206;
        A61F 13/022; A61F 13/42; A61F 2/064;
        A61F 2/07; A61F 2/2409; A61F 2/2412;
        A61F 2/2418; A61F 2/2445; A61F 2/90;
        A61F 2002/065; A61F 2005/412; A61F
            2005/417; A61F 2013/00174; A61F
            2013/00957; A61F 2013/424; A61F
        2210/0076; A61F 2230/0069; A61F
        2240/00; A61F 5/00; A61F 5/0127; A61F
        5/41; A61B 5/01; A61B 5/02055; A61B
        2562/0219; A61B 5/1118; A61B 5/0022;
        A61B 5/0205; A61B 5/681; A61B 5/002;
        A61B 5/7275; A61B 2562/0247; A61B
        5/021; A61B 5/0816; A61B 5/1117; A61B
        5/14532; A61B 5/318; A61B 5/7267;
        A61B 5/7282; A61B 5/6824; A61B
        5/411; A61B 5/4866; A61B 7/00; A61B
        5/0006; A61B 5/1112; A61B 5/389; A61B
        5/447; A61B 5/7225; A61B 5/11; A61B
        5/369; A61B 5/6891; A61B 5/1116; A61B
        5/7264; A61B 5/746; A61B 5/14542;
        A61B 5/14551; A61B 5/6801; A61B
        7/04; A61B 8/565; A61B 5/742; A61B
        5/6892; A61B 5/024; A61B 5/384; A61B
        5/026; A61B 5/6807; A61B 5/0261; A61B
        5/0008; A61B 5/02438; A61B 5/7475;
        A61B 5/1113; A61B 5/6826; A61B
        5/0533; A61B 5/4884; A61B 5/6803;
        A61B 5/053; A61B 5/743; A61B
        5/02405; A61B 8/0808; A61B 5/6804;
        A61B 5/0024; A61B 5/0531; A61B
        5/4875; A61B 5/7278; A61B 8/06; A61B
        2562/043; A61B 2560/0412; A61B 5/726;
        A61B 2560/0214; A61B 5/0537; A61B
        5/398; A61B 5/6843; A61B 5/7455; A61B
        5/0002; A61B 5/4833; A61B 5/7445;
        A61B 5/1038; A61B 5/7405; A61B
        2562/029; A61B 5/4809; A61B 5/0077;
        A61B 5/113; A61B 5/6833; A61B 5/1115;
        A61B 5/7214; A61B 5/7257; A61B 8/00;
        A61B 2562/0261; A61B 5/1114; A61B
        5/4806; A61B 5/6802; A61B 2562/02;
        A61B 5/6831; A61B 5/7465; A61B 5/00;
        A61B 5/029; A61B 5/4519; A61B
        5/6806; A61B 8/488; A61B 5/02108;
        A61B 5/25; A61B 5/445; A61B 5/686;
        A61B 2562/0214; A61B 5/165; A61B
        2560/0223; A61B 2562/0223; A61B 5/0059; A61B 5/022; A61B 5/7246; A61B
        7/045; A61B 5/4872; A61B 5/0013; A61B
        5/0833; A61B 5/395; A61B 5/112; A61B
        5/145; A61B 5/0082; A61B 5/02416;
        A61B 2560/0242; A61B 2562/0271;
        A61B 5/0031; A61B 5/721; A61B 8/56;
        A61B 5/6816; A61B 2560/0252; A61B
        5/1121; A61B 5/296; A61B 5/4023; A61B
        5/4528; A61B 5/0004; A61B 2562/164;
        A61B 5/1102; A61B 5/6829; A61B
        2560/0219; A61B 5/1128; A61B 5/0245;
        A61B 5/1036; A61B 5/33; A61B
        2503/08; A61B 5/683; A61B 5/0215;
        A61B 2560/0295; A61B 2562/12; A61B
        5/1468; A61B 5/30; A61B 5/7207; A61B
        2562/08; A61B 5/6823; A61B 5/72; A61B
        8/4472; A61B 2562/046; A61B 5/02014;
        A61B 5/0295; A61B 5/6898; A61B
        5/7203; A61B 5/031; A61B 5/4851; A61B
        5/6812; A61B 5/6822; A61B 5/7435;
        A61B 17/74; A61B 2562/063; A61B
        46/00; A61B 5/02125; A61B 5/036; A61B
        5/4812; A61B 5/6853; A61B 5/6862;
        A61B 17/80; A61B 2560/0233; A61B
        5/6808; A61B 5/1455; A61B 5/6846;
        A61B 5/6887; A61B 2560/045; A61B
        2560/0475; A61B 2562/04; A61B 5/0026;
        A61B 5/0053; A61B 5/201; A61B
        5/4839; A61B 5/6832; A61B 5/224; A61B
        5/291; A61B 2562/0233; A61B 2562/187;
        A61B 2562/247; A61B 5/0051; A61B
        5/0265; A61B 5/1124; A61B 5/14517;
        A61B 5/242; A61B 5/363; A61B 5/377;
        A61B 5/442; A61B 5/4818; A61B
        5/7271; A61B 2505/01; A61B 2560/0468;
        A61B 2562/227; A61B 5/0015; A61B
        5/086; A61B 5/1176; A61B 5/14539;
        A61B 5/316; A61B 5/4076; A61B
        5/4803; A61B 5/6838; A61B 5/747; A61B
        7/003; A61B 5/0075; A61B 5/0225; A61B
        5/0536; A61B 5/076; A61B 5/08; A61B
        5/1123; A61B 5/1135; A61B 5/282; A61B
        5/4836; A61B 5/02007; A61B 5/103;
        A61B 5/332; A61B 5/4815; A61B
        5/6828; A61B 2562/066; A61B 5/02141;
        A61B 5/14552; A61B 5/347; A61B
        5/486; A61B 5/7232; A61B 8/52; A61B
        10/0012; A61B 2018/00708; A61B
        2090/064; A61B 2560/0257; A61B
        2562/06; A61B 2562/166; A61B 5/02444;
        A61B 5/14503; A61B 5/283; A61B
        5/4088; A61B 5/4261; A61B 5/48; A61B
        7/005; A61B 7/006; A61B 18/1492; A61B
        2010/0019; A61B 2017/12004; A61B
        2018/00601; A61B 2560/0209; A61B
        2562/0257; A61B 5/015; A61B 5/02158;
        A61B 5/1126; A61B 5/14546; A61B
        5/14557; A61B 5/441; A61B 5/6805;
        A61B 17/1325; A61B 18/148; A61B
        2018/00244; A61B 2018/00589; A61B
        2018/00642; A61B 2018/00839; A61B
        2018/00982; A61B 2090/065; A61B
        2562/0204; A61B 2562/028; A61B
        5/0062; A61B 5/02; A61B 5/02042; A61B
        5/02116; A61B 5/03; A61B 5/1473; A61B 5/1495; A61B 5/412; A61B 5/6867; A61B 5/6895; A61B 8/02; A61B 90/02; A61B 90/30; A61B 17/00491; A61B 17/0057; A61B 17/12118; A61B 17/12181; A61B 17/3468; A61B 18/18; A61B 2017/00411; A61B 2017/0065; A61B 2017/00876; A61B 2017/1205; A61B 2090/376; A61B 2090/378; A61B 2505/03; A61B 2562/0215; A61B 2562/0217; A61B 2562/0238; A61B 2562/222; A61B 5/0017; A61B 5/02152; A61B 5/0255; A61B 5/1072; A61B 5/163; A61B 5/339; A61B 5/349; A61B 5/352; A61B 5/6811; A61B 5/6813; A61B 5/6815; A61B 5/725; A61B 5/74; A61B 5/749; A61B 8/4427; A61B 8/582; A61B 90/37; A61B 17/12; A61B 17/1322; A61B 18/1206; A61B 2017/00398; A61B 2018/00077; A61B 2018/00083; A61B 2018/0022; A61B 2018/00666; A61B 2018/0072; A61B 2018/00755; A61B 2018/00827; A61B 2018/00875; A61B 2018/1246; A61B 2034/105; A61B 2090/309; A61B 2503/10; A61B 2503/12; A61B 2560/0228; A61B 2560/0443; A61B 2560/0456; A61B 5/0048; A61B 5/02028; A61B 5/1075; A61B 5/372; A61B 5/383; A61B 5/4343; A61B 5/4362; A61B 5/4566; A61B 5/4848; A61B 50/13; A61B 90/90; A61B 90/92; A61B 17/135; A61B 17/1355; A61B 17/320036; A61B 5/302; A61B 5/366; A61B 5/378; A61B 5/413; A61B 5/4504; A61B 5/4547; A61B 5/4561; A61B 5/4821; A61B 5/4842; A61B 5/6825; A61B 5/684; A61B 5/6841; A61B 5/6848; A61B 5/6849; A61B 5/6861; A61B 5/6868; A61B 5/6869; A61B 5/6873; A61B 5/6885; A61B 5/7235; A61B 5/7239; A61B 6/0407; A61B 6/0487; A61B 6/107; A61B 6/12; A61B 6/481; A61B 8/0883; A61B 8/0891; A61B 8/10; A61B 8/481; A61B 8/5261; A61B 90/14; A61B 90/70; A61B 18/22; A61B 2017/00026; A61B 2017/0003; A61B 2017/00221; A61B 2017/00871; A61B 2017/22001; A61B 2018/00791; A61B 2018/205; A61B 2503/02; A61B 2560/0247; A61B 2560/0462; A61B 2562/0209; A61B 2562/0252; A61B 2562/125; A61B 2562/16; A61B 5/0011; A61B 5/0064; A61B 5/02233; A61B 5/0285; A61B 5/032; A61B 5/038; A61B 5/05; A61B 5/065; A61B 5/073; A61B 5/0826; A61B 5/1101; A61B 5/1104; A61B 5/14521; A61B 5/1459; A61B 5/225; A61B 5/228; A61B 5/259; A61B 5/392; A61B 5/4082; A61B 5/417; A61B 5/4266; A61B 5/4552; A61B 5/4878; A61B 5/682; A61B 5/68335; A61B 5/6852; A61B 5/6865; A61B 5/6893; A61B 5/6894; A61B 5/7221; A61B 5/741; A61B 8/04; A61B 8/0816; A61B 8/4227; A61B 8/4236; A61B 8/58; A61B 90/06; A61B 90/40; A61B 90/94; A61B 90/98; A61B 1/018;

A61B 10/0064; A61B 17/072; A61B 17/07207; A61B 17/085; A61B 17/1128; A61B 17/1155; A61B 17/12022; A61B 17/12031; A61B 17/1204; A61B 17/12109; A61B 17/12136; A61B 17/12168; A61B 17/12177; A61B 17/122; A61B 17/205; A61B 17/22; A61B 17/2251; A61B 17/3403; A61B 18/02; A61B 18/04; A61B 18/12; A61B 18/1445; A61B 18/245; A61B 2010/0016; A61B 2017/00017; A61B 2017/00115; A61B 2017/00119; A61B 2017/00199; A61B 2017/0046; A61B 2017/00535; A61B 2017/00544; A61B 2017/00561; A61B 2017/00734; A61B 2017/00809; A61B 2017/00867; A61B 2017/00911; A61B 2017/07221; A61B 2017/07257; A61B 2017/07271; A61B 2017/07285; A61B 2017/22042; A61B 2017/2927; A61B 2017/2933; A61B 2017/320093; A61B 2017/3413; A61B 2018/00005; A61B 2018/00023; A61B 2018/00345; A61B 2018/00517; A61B 2018/00541; A61B 2018/00577; A61B 2018/00595; A61B 2018/00613; A61B 2018/0063; A61B 2018/00892; A61B 2018/1273; A61B 2018/1455; A61B 2018/1467; A61B 2018/1861; A61B 2034/2051; A61B 2034/2059; A61B 2034/301; A61B 2090/066; A61B 2090/0808; A61B 2090/0811; A61B 2090/3954; A61B 2217/005; A61B 2217/007; A61B 2218/002; A61B 2560/0406; A61B 2560/06; A61B 2562/0276; A61B 2562/14; A61B 2562/168; A61B 2562/18; A61B 2562/182; A61B 34/30; A61B 34/32; A61B 34/37; A61B 5/0028; A61B 5/0073; A61B 5/02208; A61B 5/02225; A61B 5/02241; A61B 5/02411; A61B 5/062; A61B 5/091; A61B 5/107; A61B 5/1071; A61B 5/1079; A61B 5/1106; A61B 5/1107; A61B 5/1122; A61B 5/1125; A61B 5/14507; A61B 5/1477; A61B 5/1486; A61B 5/14865; A61B 5/162; A61B 5/202; A61B 5/22; A61B 5/24; A61B 5/256; A61B 5/265; A61B 5/266; A61B 5/28

USPC ....................................................... 604/305
See application file for complete search history.

(56)                   References Cited

U.S. PATENT DOCUMENTS

| | | | |
|---|---|---|---|
| 6,211,426 B1 | 4/2001 | Abrams | |
| 7,014,630 B2 * | 3/2006 | Rosati | A61F 13/025 |
| | | | 604/304 |
| 7,625,117 B2 * | 12/2009 | Haslett | A61B 5/01 |
| | | | 374/111 |
| 7,813,807 B2 | 10/2010 | Franklin | |
| 8,338,526 B2 * | 12/2012 | Kanai | B05D 1/322 |
| | | | 525/308 |
| 8,460,257 B2 | 6/2013 | Locke et al. | |
| 10,143,081 B2 | 11/2018 | Wang et al. | |
| 2008/0306407 A1 | 12/2008 | Taylor | |
| 2010/0112087 A1 | 5/2010 | Harrison et al. | |
| 2011/0257610 A1 * | 10/2011 | Franklin | A61F 13/0203 |
| | | | 141/4 |

(56) References Cited

U.S. PATENT DOCUMENTS

| | | | | |
|---|---|---|---|---|
| 2011/0257617 | A1 | 10/2011 | Franklin | |
| 2012/0059301 | A1 | 3/2012 | Franklin | |
| 2017/0347940 | A1* | 12/2017 | Carr | A61B 5/145 |
| 2017/0348155 | A1 | 12/2017 | Duesterhoft et al. | |
| 2017/0348156 | A1* | 12/2017 | Duesterhoft | A61B 5/0002 |
| 2018/0000651 | A1 | 1/2018 | Pan et al. | |
| 2018/0333288 | A1 | 11/2018 | Squires et al. | |
| 2019/0000324 | A1 | 1/2019 | Laugaard Nielsen | |
| 2019/0192066 | A1 | 6/2019 | Schoess et al. | |
| 2019/0262495 | A1 | 8/2019 | Bruce et al. | |
| 2019/0290496 | A1 | 9/2019 | Brownhill et al. | |
| 2019/0314420 | A1 | 10/2019 | Carter et al. | |
| 2020/0023102 | A1 | 1/2020 | Powell | |
| 2020/0289347 | A1* | 9/2020 | Gowans | A61M 1/916 |

OTHER PUBLICATIONS

Boyko TV, et al., Review of the Current Management of Pressure Ulcers. Adv Wound Care (New Rochelle). 2018;7(2):57-67.

Gould L, et al., Chronic wound repair and healing in older adults: current status and future research. J Am Geriatr Soc. 2015;63(3):427-438.

Gorecki C, et al., Impact of pressure ulcers on quality of life in older patients: a systematic review. J Am Geriatr Soc. 2009;57(7):1175-1183.

Coleman S, et al., A new pressure ulcer conceptual framework. J Adv Nurs. 2014;70(10):2222-2234.

Schoonhoven L, et al., The prevalence and incidence of pressure ulcers in hospitalised patients in the Netherlands: a prospective inception cohort study. Int J Nurs Stud. 2007;44(6):927-935.

Vowden KR, et al., The prevalence, management, equipment provision and outcome for patients with pressure ulceration identified in a wound care survey within one English health care district. J Tissue Viability. 2009;18(1):20-26.

Gould LJ, et al., Pressure ulcer summit 2018: An interdisciplinary approach to improve our understanding of the risk of pressure-induced tissue damage. Wound Repair Regen. 2019;27(5):497-508.

Clark M, et al., Systematic review of the use of prophylactic dressings in the prevention of pressure ulcers. Int Wound J. 2014;11(5):460-471.

Cornish L., The use of prophylactic dressings in the prevention of pressure ulcers: a literature review. Br J Community Nurs. 2017;22(Sup6):S26-S32.

Moore ZE, et al., Dressings and topical agents for preventing pressure ulcers. Cochrane Database Syst Rev. 2018;12:CD009362.

Walker RM, et al., Foam dressings for treating pressure ulcers. Cochrane Database Syst Rev. 2017;10:CD011332.

Reenalda J, et al., Analysis of healthy sitting behavior: interface pressure distribution and subcutaneous tissue oxygenation. J Rehabil Res Dev. 2009;46(5):577-586.

National Pressure Injury Advisory Panel Support Surface Standards Initiative (S3I) Terms and Definitions Related to Support Surfaces Ver. Jan. 29, 2007 Revised: Dec. 27, 2018; Nov. 19, 2019.

* cited by examiner

FIG. 2A                          FIG. 2B

SENSOR ENABLED THERAPEUTIC WOUND AND TISSUE MONITOR

BACKGROUND

This application is based upon U.S. Provisional Application Ser. No. 63/339,567 filed May 9, 2022 the complete disclosure of which is hereby expressly incorporated by this reference.

Pressure injury, also known as pressure ulcers, decubitus ulcers, and bed sores, develop as a result of pressure on tissues in combination with physiologic events and external conditions. Generally, pressure injuries are localized damage to the skin and underlying soft tissue which usually occur over a bony prominence or are related to the use of a medical or other device. Pressure injuries negatively affect the quality of life for millions of people, especially older individuals with immobility, and are a substantial cause of morbidity and societal burden worldwide.

The etiology of pressure injury development is multifactorial involving both extrinsic (lying on hard surface, poor skin hygiene, patient restraints, medical devices etc.) and intrinsic (diabetes, smoking, malnutrition, spinal cord injury etc.) factors. Mechanical boundary conditions like magnitude, duration and type of the mechanical load, pressure, shear, and friction contribute to the damage of epidermal and dermal skin layers and changes in interstitial fluid flow leading to altered metabolic equilibrium resulting in tissue death. Strategies to prevent pressure injuries should consider the microclimate and biomechanics of the soft tissue interacting with direct pressure, shear forces, and friction that can cause tissue distortion and deformation.

Many wound dressings are available to clinicians to help treat pressure injury, and reportedly these devices vary significantly in the degree of effectiveness. Dressing manufacturers who historically only reported the properties of their dressing design as an adjunct to promote wound healing are now beginning to jump onboard the pressure ulcer risk reduction bandwagon. Various dressing materials such as alginate, foam, gauze, honey, hydrocolloid, hydrogel, silver, and transparent film have been studied in the last decade for the management of pressure injury, and clinical and cost-effective comparisons of various wound dressings are documented in the literature.

In the past, some have suggested that the prophylactic application of materials, primarily foam based wound dressings, over certain anatomical locations may help to mitigate forces which contribute to the formation of pressure injuries. The data suggests that utilizing certain types of wound dressings in this fashion reduces pressure forces and thus may decrease onset of pressure injury in certain patients. One problem with these types of wound dressings is that they are only passive in nature. They absorb fluid from the wound and protect the wound, but they do not provide an active therapeutic treatment to help the wound heal.

Some types of wound dressing include electric sensors and components which measure and communicate information about the patient and/or the wound. These types of dressings are very helpful in gathering information and alerting caregivers to potential problems with the patient. However, one problem with these types of wound dressings is that they fail to conform to the twisting, turning, and stretching movement of the user's body. As a result, these types of dressings are uncomfortable and often become unintentionally shifted away from the location of the wound. There is therefore a need for an improved device which overcomes these and other problems in the prior art.

SUMMARY OF THE PRESENT DISCLOSURE

One aspect of the present disclosure relates to a therapeutic device used for wound, ulcer, skin and tissue (WUST) monitoring. The device includes a flexible-stretchable film-based circuit board controlled by a processor, one or more sensors, and a wireless transceiver using ISM bands. In some embodiments the circuit board is made from or printed on a flexible and elastic thermoplastic film that allows for the single-, double- or multi-layered soldering of electronic components on traces with soldered connections that can stretch and rebound back to original shape. The film allows components to be over molded with the same material to protect the patient and components while leaving some sensors open to the environment. The one or more sensors are configured to detect or measure certain physical properties near the wound and communicate the data to the processor. The processor is programmed with specific algorithms which allow the device to determine whether alarms or other notifications should be sent to third parties through the wireless transceiver. The third parties may include doctors, nurses, or other caregivers. The one or more sensors may include sensors configured to measure or detect the following physical properties of the patient or the wound: acceleration, chemical, current, conductivity, heart rate, movement (X,Y,Z), genomic, gaseous (including methane, carbon dioxide, nitrogen dioxide, oxygen, ozone), metabolic, motion, moisture, optical (including ultraviolet, visible, infrared radiation, colorimetric), pressure, pH, perfusion, shear, strain, temperature, voltage used singularly or in combination to monitor WUST characteristics, metabolic profiles and/or genomic signatures related to development, deterioration or healing associated with dermal compromise. In some embodiments the sensors are positioned between an external layer and a perforated inner wound layer. The perforated inner wound layer includes one or more openings configured to allow fluid and gas from the wound to easily reach the sensors. In some embodiments the device further includes a gaseous reservoir configured to cushion the wound and/or therapeutically expel a healing gas toward the wound. The gaseous reservoir may be positioned above (toward the external layer) the sensors. The gaseous reservoir contains a gas which may be rich in oxygen, nitric oxide, other suitable therapeutic gas, or combinations of several gases. In some embodiments a portion of the wall of the gaseous reservoir is a semipermeable membrane configured to allow the gas to slowly be expelled from the gaseous reservoir toward the wound. In other embodiments, the gaseous reservoir is sealed to form a pocket of gas which functions as a cushion for the wound.

Another aspect of the present disclosure relates to a therapeutic device used for WUST monitoring which comprises an external layer impermeable to gas and moisture with a periphery that adheres to a user's skin about a wound and an internal layer with a periphery adhered to the external layer creating a gaseous reservoir between the external and internal layers. In some embodiments the internal layer is semipermeable to allow a gas, such as oxygen or nitric oxide, to diffuse from the gaseous reservoir toward the wound. The semipermeable internal layer also allows moisture from the user's wound to be absorbed into the dressing. A spacer layer, which may be a foam layer, separates the external layer and the internal layer and is configured to absorb fluid and wound exudate. In other embodiments the gaseous reservoir is sealed to form a pocket of gas which functions as a cushion for the wound. A flexible, bendable and stretchable, film-based circuit board is positioned below the internal layer (farther from the external layer) and includes a processor, at least one sensor, and a wireless transceiver. A perforated inner wound layer is positioned below the circuit board so that the circuit board is between the perforated inner wound layer and the internal layer. and the perforated inner wound layer includes apertures to allow diffusion of fluid, gas and other wound transudates to enter the device and contact the sensors and an adhesive periphery for providing a seal between the external layer and the internal layer.

Another aspect of the present disclosure relates to a therapeutic device for sensing and communicating information about a user's wound, ulcer, skin and tissue (WUST). The device includes a gaseous reservoir having a periphery that is configured to adhere to a user's skin about a wound on the user's skin. The gaseous reservoir has an external layer that is impermeable to gas and moisture, an internal layer having a periphery adhered to the external layer, and a spacer layer disposed between the external layer and the internal layer. The spacer layer may be an absorbent foam layer. The spacer layer creates a space between the external layer and the internal layer and provides some structure for the gaseous reservoir. The space between the layers allows an amount of gas, which may be ambient air, oxygen, nitric oxide, other suitable gas or any combination of gases to be contained within the space between the external layer and the internal layer. In one embodiment the internal layer is semipermeable to allow a portion of the amount of gas to diffuse from the gaseous reservoir toward the user's wound, and to allow an amount moisture to be transferred from the user's wound to the spacer layer within the gaseous reservoir. The spacer layer has a thickness and is configured to absorb the amount of moisture transferred from the user's wound to the gaseous reservoir. In other embodiments the gaseous reservoir is sealed to form a pocket of gas which functions as a cushion for the wound. A bendable, flexible and stretchable, film-based circuit board is located on the internal layer on a surface away from the external layer and includes a processor, at least one sensor, and a wireless transceiver. A perforated inner wound layer is positioned below the circuit board. The perforated inner wound layer comprising a plurality of apertures to allow diffusion of fluid, gas and other wound transudates to enter the device and contact the sensors. The perforated inner wound layer also comprising an adhesive periphery for providing a seal between the external layer and the internal layer.

Yet another aspect of the present disclosure relates to a therapeutic device used for wound, ulcer, skin and tissue (WUST) monitoring. The device includes an outer layer that is impermeable to gas and moisture, an internal layer having a periphery adhered to an underside of the outer layer thereby creating a gaseous reservoir between the layers containing an amount of gas, such as oxygen or nitric oxide, between the outer layer and the internal layer. A spacer layer, which may be an absorbent foam layer is disposed between the outer layer and the internal layer, the spacer layer having a thickness and configured to absorb fluid and wound exudate from a user's wound, whereby the thickness creates a space between the outer layer and the internal layer. A bendable, flexible and stretchable, film-based circuit board is disposed on the internal layer on a surface away from the outer layer. The circuit board includes a processor, at least one sensor, and a wireless transceiver. A perforated inner wound layer positioned below the circuit board is coupled at its outer periphery to the outer layer. The perforated inner wound layer comprising a plurality of apertures to allow diffusion of fluid, gas and other wound transudates to enter the device and contact the sensors, and an adhesive periphery for providing a seal between the outer layer and the internal layer. The perforated inner wound layer further comprises an adhesive wound surface configured to adhere to a user's skin about a wound.

These and other aspects, objects, and features of the present disclosure will be understood and appreciated by those skilled in the art upon studying the following specification, claims, and appended drawings.

DETAILED DESCRIPTION

Figure 1:
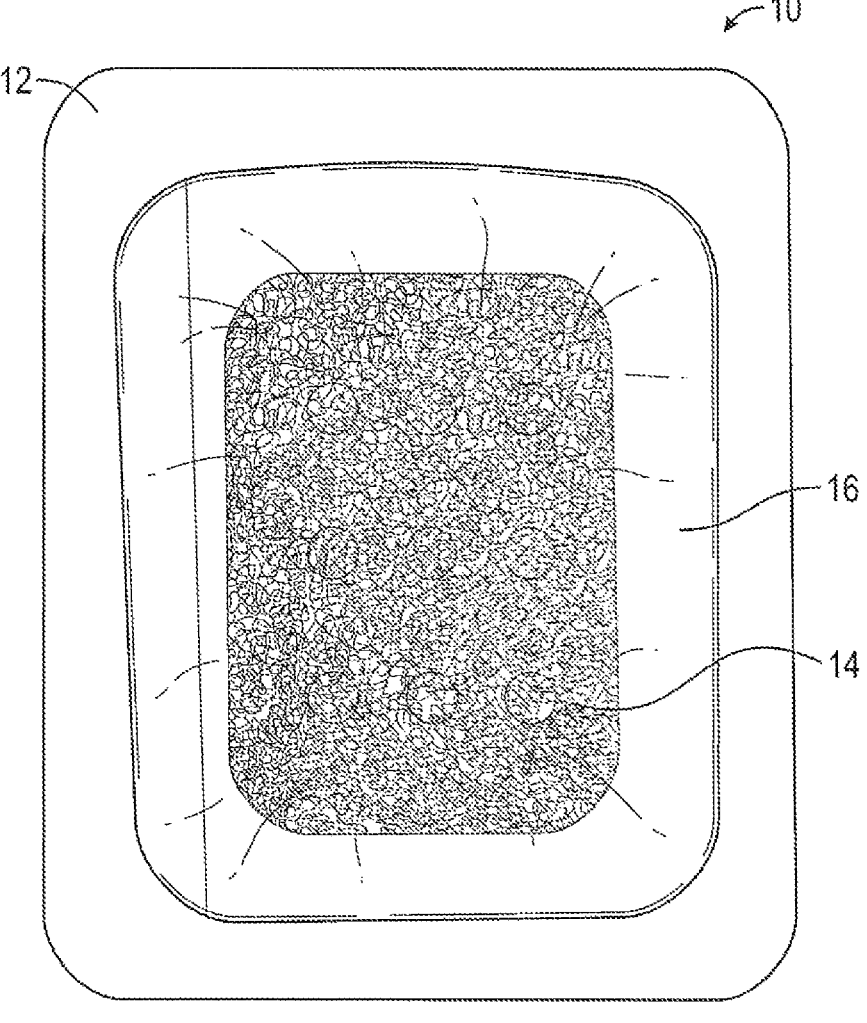
FIG. 1 is a top view of a therapeutic device of an embodiment.
Figure 2:
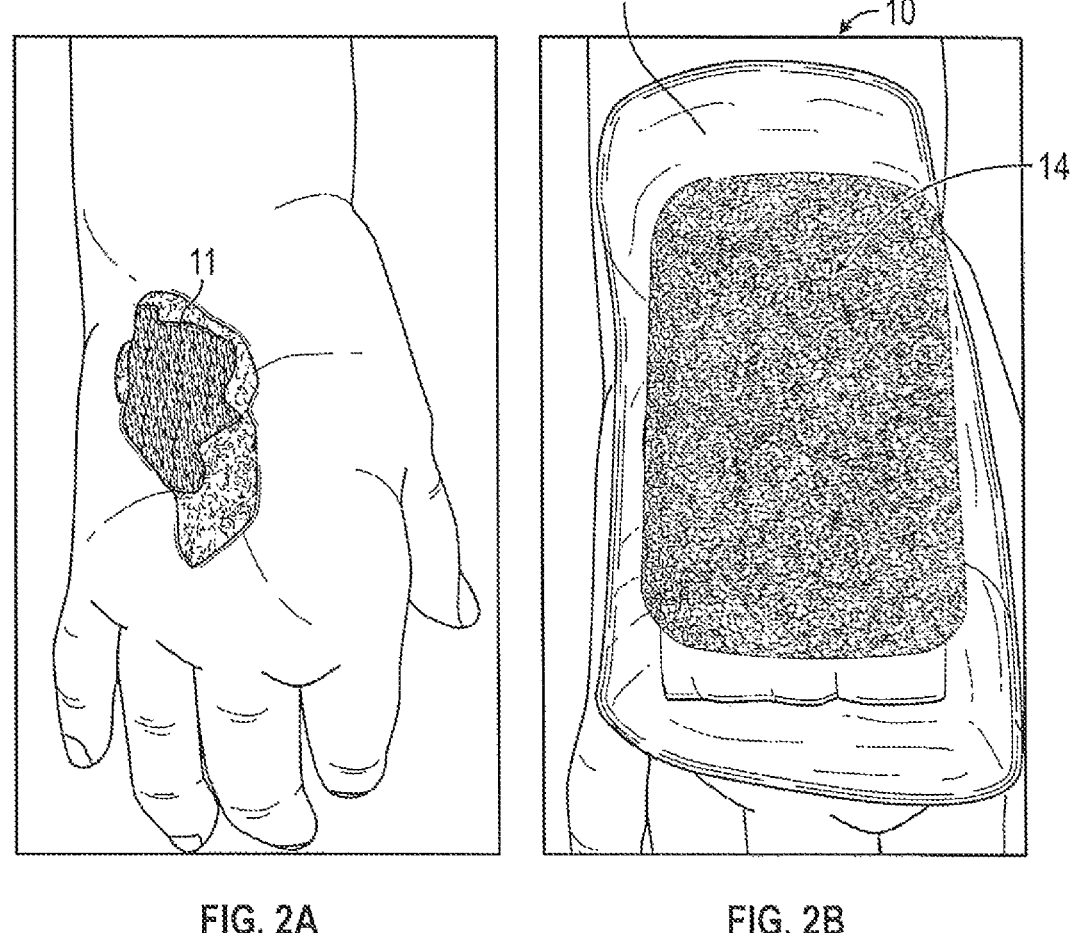
FIG. 2A is a top view showing a wound on a user's hand.
FIG. 2B is a top view showing the wound from FIG. 2A covered by an embodiment of the therapeutic device.

For purposes of description herein, the terms "above" and "below" and derivatives thereof shall relate to the disclosure as oriented in FIG. 5. However, it is to be understood that the disclosure may assume various alternative orientations and may be attached to a user in any suitable orientation, The detailed description and attached figures generally describe a therapeutic device 10 used for wound, ulcer, skin, and tissue (WUST) monitoring. FIG. 1 generally shows a top view of the therapeutic device 10. FIG. 2A shows a wound 11 on a patient's hand. FIG. 2B shows the therapeutic device 10 covering the wound 11. The therapeutic device 10 generally includes an external layer 12, an internal layer 16, and a spacer layer 14 positioned in a gaseous reservoir between the external layer 12 and the internal layer 16. One or more sensors 22 are positioned below (toward the wound when the device 10 is in use) the gaseous reservoir. The sensors 22 are configured to measure one or more physical properties at or near the wound 11. In some embodiments a perforated inner wound layer 18 is positioned below the sensors 22.

Figure 3:
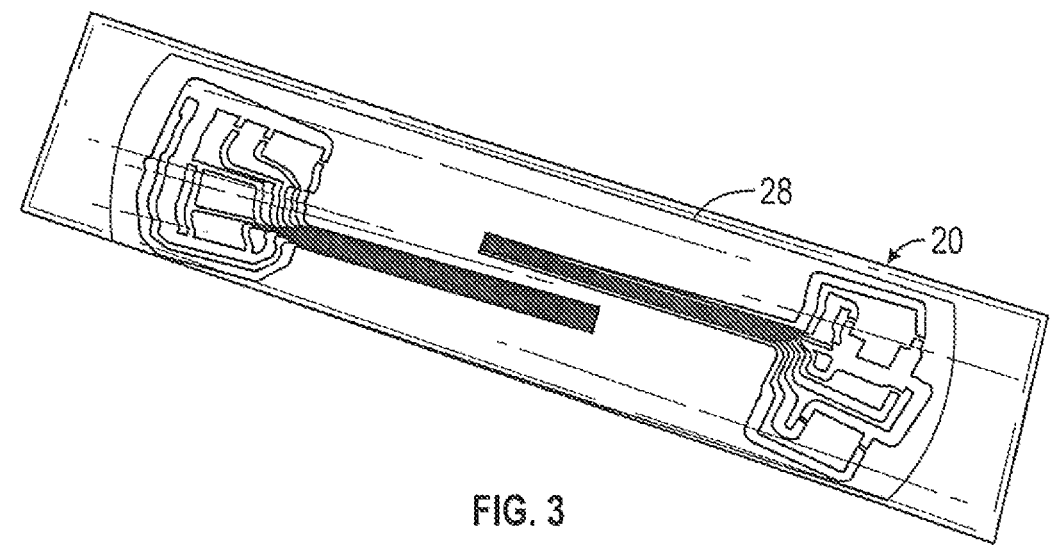
FIG. 3 is a top view showing a circuit board.
Figure 4:
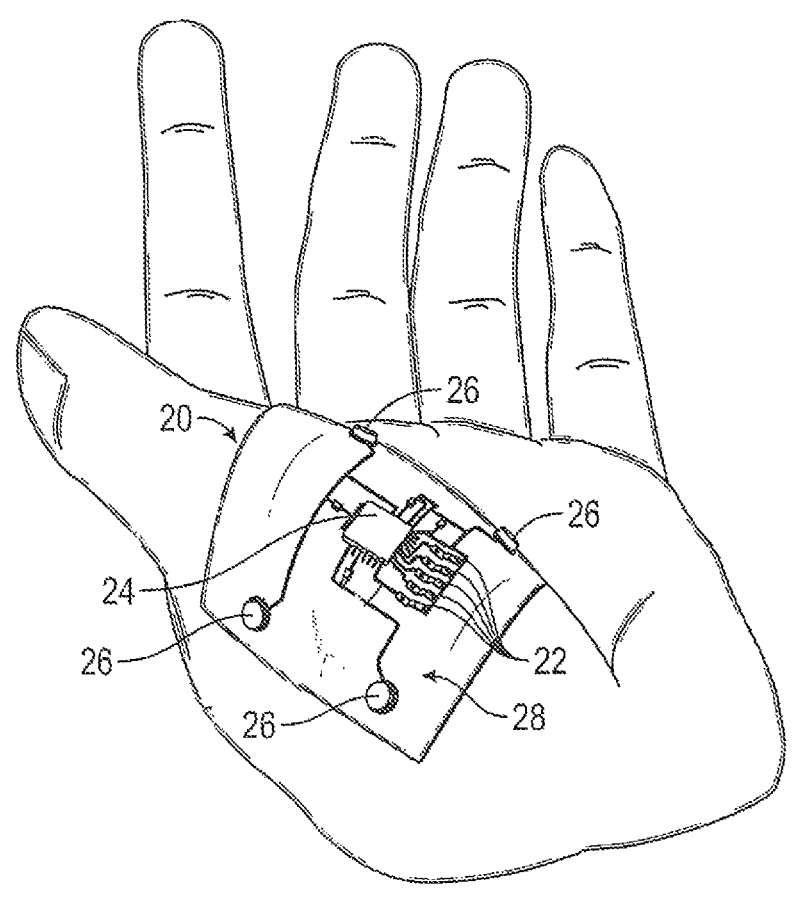
FIG. 4 is a perspective view showing a circuit board, sensors, processor, and transceiver attached to a user's hand.

The sensors 22 are combined with a film-based circuit board 20 comprising a plurality of electrical components, as described herein. FIGS. 3 and 4 show embodiments of the circuit board 20 and the electrical components in communication therewith. In some embodiments the film-based circuit board 20 is bendable and stretchable allowing it to conform to the contours and movements of the user's body. For example, the circuit board 20 may be positioned on a stretchable, flexible, elastomeric, thermoplastic film. The circuit board 20 is controlled by a processor 24 which is configured to receive data from the one or more sensors 22. A wireless transceiver 26 is configured to transmit data to other devices, such as phones, tablets, and computers. In some embodiments, the wireless transceiver 26 uses a radio frequency band commonly used for industrial, scientific, and medical purposes (ISM bands) to transmit data to doctors or nurses at a nurse's station in a hospital or nursing home. In some embodiments the processor 24 is programmed with algorithms configured to determine whether the data received from the sensors 22 falls within certain predetermined ranges. In the event the data falls within these ranges, the processor 24 is configured to communicate signals to certain individuals, computers, or alarms to alert third parties about the condition of the user/wound. The processor 24 may be powered by an on-board battery that may be rechargeable or replaceable.

The circuit board 20 may be comprised of a durable, flexible, bendable and stretchable material. The material allows the circuit board 20 to bend, twist, and stretch along with the movement of the user while retaining little to no hysteresis and ensuring that all electrical contacts and circuits remain in place and functional. For instance, the physical properties of the material which allow for the necessary three-dimensional stretching and deformability need greater than 98% recovery in returning to the original shape after the distortion forces are removed. The circuit board 20 may be printed on a stretchable, bendable thermoplastic film 28 that allows for the single-, double- or multi-sided soldering of electronic components 22, 26 on traces 30 with soldered connections that can stretch and rebound back to original shape. The film 28 allows components 22 to be over molded with the same material to protect the patient and the components while leaving one or more sensors 22 open to the environment.

The thermoplastic film 28 may be formed by extruding a molten polymeric composition onto a chill roller, where it is immediately cooled to make a solid film. Processing of the film 28 includes a variety of steps, including heating, cooling and stretching to produce a final film product having a thickness of about 72 times less than the initial thickness. Stretching in the machine direction (MD) forms a highly oriented thin gauge film, which is referred to as machine direction orientation (MDO). MDO may be useful, however, may also result in qualities such as reduced cross-directional (CD) tensile strength, impact strength, tear strength and slow puncture resistance, particularly in thinner films.

The thermoplastic film may be liquid impervious, vapor permeable (e.g., breathable), bondable to other layers of the therapeutic device 10, and have sufficient physical strength to be processed into a finished article. Breathable films having a sufficient strength and basis weight may be particularly useful for products that need to release odors resulting from the manufacturing process.

As noted above, the flexible circuit board 20 may include one or more sensors 22. The sensors 22 may be configured to sense data (analog or digital) related to one or more of the following physical properties: acceleration, chemical, current, conductivity, heart rate, movement (x,y,z coordinates), genomic, gaseous (including methane, carbon dioxide, nitrogen dioxide, oxygen, ozone), metabolic, moisture, optical (including ultraviolet, visible, infrared radiation, and colorimetric light bands), pressure, pH, perfusion, shear, strain, temperature, and voltage sensors. These sensors 22 may be either used singularly or in combination to monitor WUST characteristics, metabolic profiles and/or genomic signatures related to development, deterioration, or healing associated with dermal compromise. Continuous and local processor 24 control of sensor data is incorporated into specific algorithms allowing real-time alarms, control and notification may be sent using wireless Industrial, Scientific, and Medical (ISM) frequency band communications. The sensors 22 and processor 24 may be powered by an on-board battery that is rechargeable (either wirelessly or via a connector that is accessible by a user or practitioner) or replaceable.

The one or more sensors 22 may be included as a component within the therapeutic device 10 that is attached to a user at a location that may be injured such as an open wound. The sensors 22 may be combined with the therapeutic device 10 below the gaseous reservoir (farther from the external layer 12) to allow the sensors 22 to receive gas, liquid, temperature, and other data directly from (or proximal to) the wound 11. The therapeutic device 10 is typically attached to the user by an adhesive that is safe for use on human skin.

Figure 5:
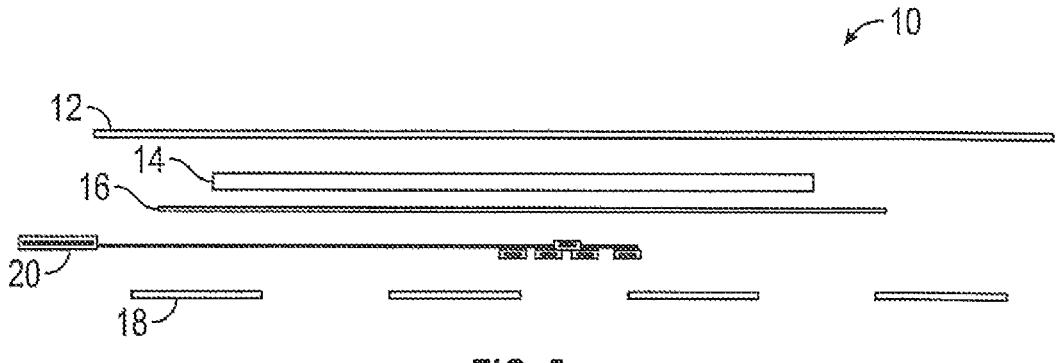
FIG. 5 is an exploded side view showing the components of an embodiment of the therapeutic device.
Figure 6:
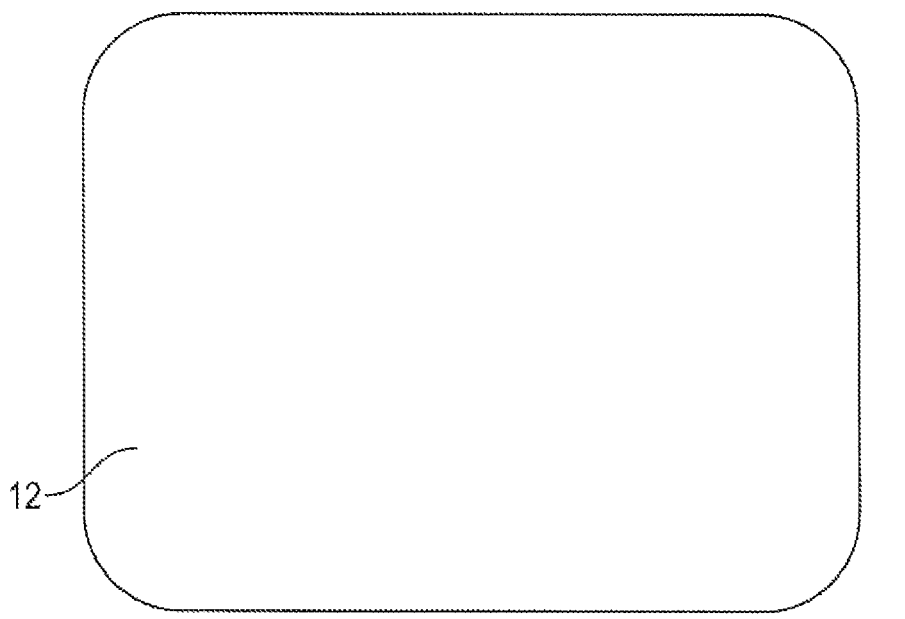
FIG. 6 is a bottom view of an external or outer layer of an embodiment of the therapeutic device.
Figure 7:
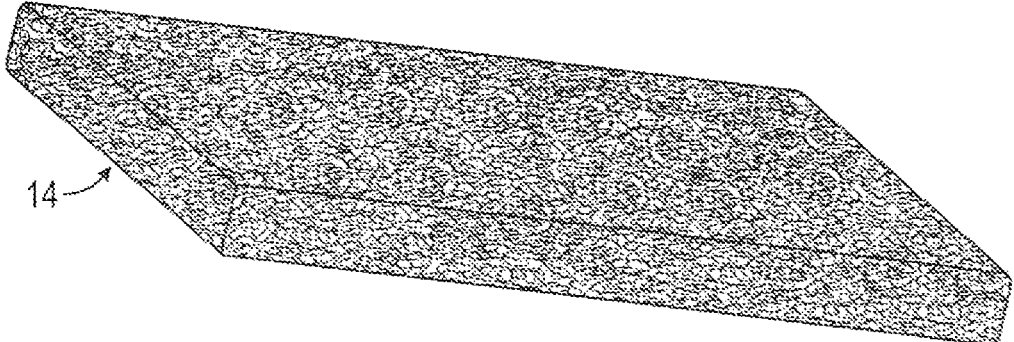
FIG. 7 is a perspective view of a foam layer of an embodiment of the therapeutic device.
Figure 8:
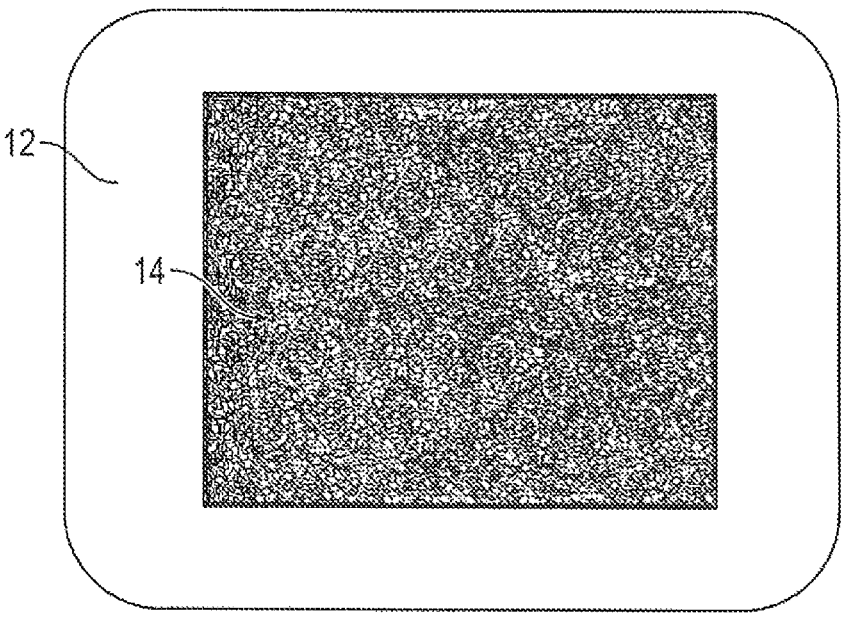
FIG. 8 is a bottom view of the foam layer of an embodiment of the therapeutic device as positioned over the external layer.
Figure 9:
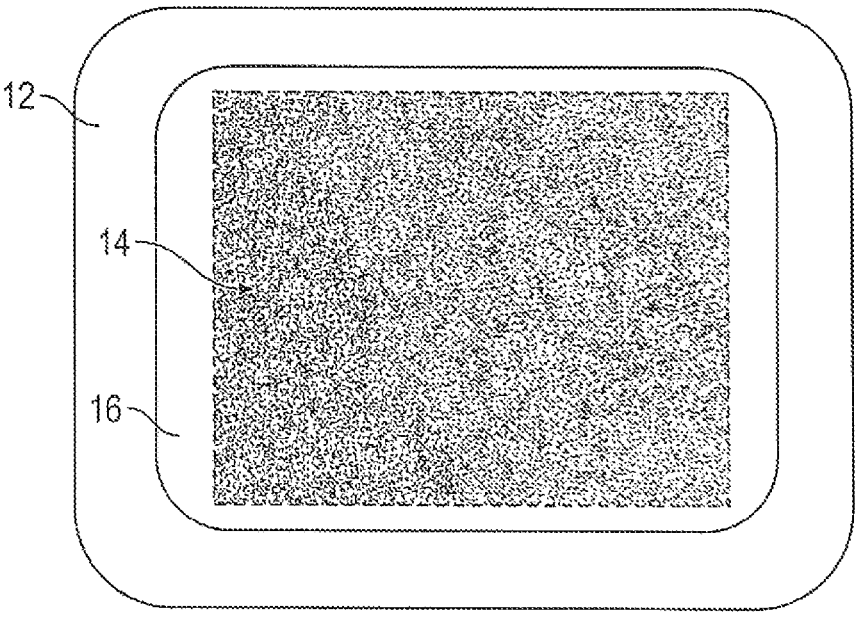
FIG. 9 is a bottom view showing the foam layer of an embodiment of the therapeutic device positioned between the internal layer and the external layer.
Figure 11:
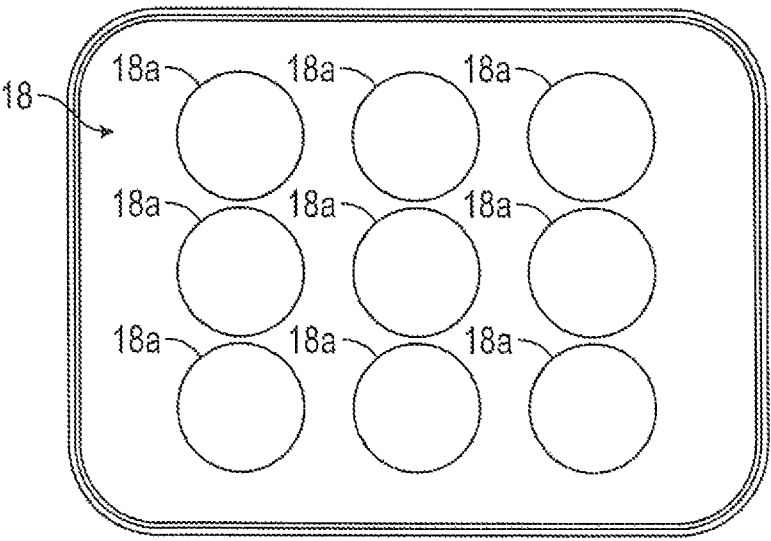
FIG. 11 is a bottom view of a perforated inner wound layer of an embodiment of the therapeutic device.
Figure 12:
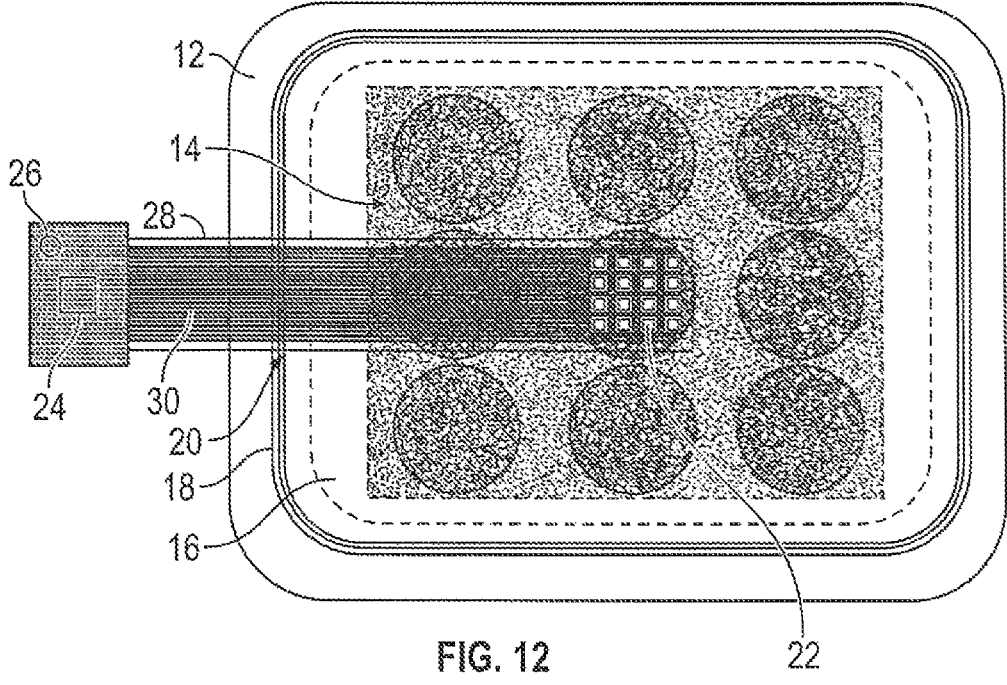
FIG. 12 is a bottom view an embodiment of the therapeutic device.

FIG. 5 shows an exploded view of the layers and components of an embodiment of the therapeutic device 10. FIGS. 6-12 show the different layers and components of the therapeutic device 10 alone and in combination illustrating how the layers and components of the therapeutic device 10 may be constructed. As shown, the therapeutic device 10 includes an external layer 12, an internal layer 16, and a spacer layer 14 positioned in a gaseous reservoir between the external layer 12 and the internal layer 16. FIG. 6 shows the external layer 12. The external layer 12 is made of a material that is impermeable to gas and moisture and provides protection for the wound 11 and the internal parts of the therapeutic device 10. In use, the external layer 12 is typically farthest from the wound. The internal layer 16 faces toward the wound and it may be semipermeable to fluids (liquids and gases) in some embodiments and impermeable to fluids in other embodiments. The spacer layer 14 is shown in FIG. 7 and may be made or foam or other suitable resilient absorbent material. The spacer layer 14 serves as a spacer between the external layer 12 and the internal layer 16, while at the same time absorbing fluid and wound exudate. FIG. 8 shows the spacer layer 14 positioned over the external layer 12. The circuit board 20 may be positioned below the internal layer 16 (toward the wound 11 when in use) to ensure the sensors 22 are proximate to the wound 11 for collecting data. In some embodiments the circuit board 20 is located on an inner surface of internal layer 16 (the surface away from the spacer layer 14 and the external layer 12). In some embodiments a perforated inner wound layer 18 is positioned below the circuit board 20. The perforated inner wound layer 18 has a periphery adhered to the external layer 12 around or about the internal layer 16 as best shown in FIG. 12.

As mentioned above and as shown in FIG. 9, the internal layer 16 has a portion (which may be around its periphery) that is sealed with a portion of the external layer 12 to create a gaseous reservoir between the two layers 12, 16. The spacer layer 14 is shown between the two layers 12, 16 in this FIG. 9. The gaseous reservoir may be rich in oxygen, carbon dioxide, nitrogen dioxide, ozone, nitric oxide, ambient air, or any other suitable gas capable of therapeutically healing wounds. The spacer layer 14 provides structure for the gaseous reservoir and helps prevent the layers 12, 16 from collapsing together, which could result in the rapid and premature release of gas.

In some embodiments the internal layer 16 is (or comprises) a semipermeable membrane that allows fluids to pass through. The semipermeable membrane of the internal layer 16 is configured to allow the gas within the gaseous reservoir to diffuse from the gaseous reservoir toward the wound 11. Oxygen and other gases have a therapeutic effect on wounds and help contribute to healing. The semipermeable membrane may be sealed after manufacture and during transport and storage to retain the gas in the gaseous reservoir. Then, the semipermeable membrane may be opened immediately prior to application on a user's wound to allow the diffusion of gas from the gaseous reservoir toward the wound. Alternatively, the therapeutic device 10 may be stored and shipped in a sealed container rich in the desired gas so the gas from the container passes through the semipermeable membrane into the gaseous reservoir. The gas remains in the gaseous reservoir until the device 10 is removed from the container, at which time the gas slowly diffuses from the reservoir. The semipermeable nature of the internal layer 16 also allows moisture from the wound to be absorbed by the absorbent 14 and wicked away from the wound into the gaseous reservoir.

In other embodiments the internal layer 16 is impermeable to fluids such that the gas in the gaseous reservoir is permanently sealed in the reservoir. In this embodiment the gaseous reservoir is sealed to form a pocket of gas which functions as a cushion for the wound. Any suitable gas may be used to fill the gaseous reservoir and the gas does not need to have any therapeutic effect on the wound since the gas remains in the reservoir.

Figure 10:
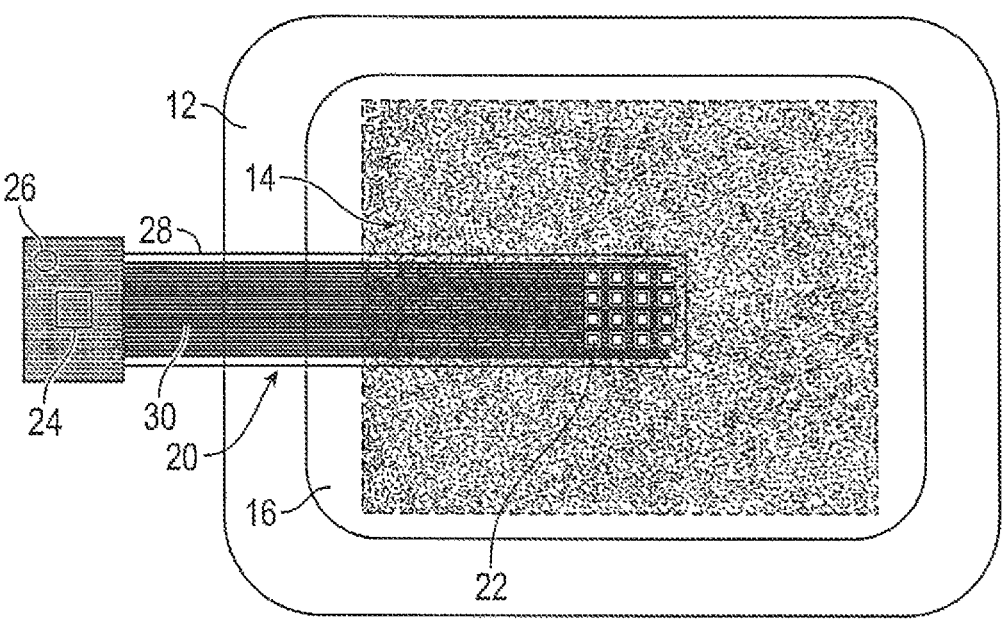
FIG. 10 is a bottom view showing a circuit board of an embodiment of the therapeutic device as attached to the internal layer.

Looking now at FIG. 10, in some embodiments the flexible circuit board 20 is attached on the bottom (opposite side from the external layer 12, toward the wound) of the internal layer 16. The flexible circuit board 20 includes sensors 22 which may be configured in an array formation as shown, or may be configured in any other configuration as needed or desired by a practitioner. The sensors 22 are attached to the flexible thermoplastic film 28 and the traces 30. The traces 30 lead to the processor 24 and wireless transceiver(s) 26 that may extend beyond the perimeter of the bandage portion of the therapeutic device 10 for better communication.

Looking at FIGS. 11 and 12, below flexible circuit board 20 (closer to the wound when in use) is a perforated inner wound layer 18 having one or more perforations 18*a*. The perforated inner wound layer 18 overlaps the internal layer 16 and provides for a seal between the internal layer 16 and the external layer 12, thus helping to seal the gaseous reservoir. The perforated inner wound layer 18 may include one or more openings 18*a*. The openings 18*a* allow fluid, gas, heat, and other physical characteristics from the wound 11 to readily reach the sensors 22 without requiring the sensors 22 to be in direct communication with the wound 11. The openings 18*a* also allow gas to defuse from the gaseous reservoir toward the wound 11 and moisture to be absorbed by the absorbent layer 14.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

The invention claimed is:

1. A therapeutic device for wound monitoring, said device comprising:

an external layer that is impermeable to gas and moisture, the external layer configured to adhere to a user's skin about a wound on the user's skin;

an internal layer having a periphery adhered to the external layer thereby creating a gaseous reservoir containing an amount of gas between the external layer and the internal layer, the internal layer comprising a semipermeable portion configured to allow a portion of the amount of gas to diffuse from the gaseous reservoir;

a spacer layer disposed between the external layer and the internal layer, the spacer layer having a thickness and configured to absorb moisture from the wound; and a bendable, flexible, and stretchable, film-based circuit board disposed below the internal layer, the circuit board comprising a processor, at least one wound monitoring sensor that detects or measures physical properties at or proximate the wound and communicates data to the processor, and a wireless transceiver.

2. The therapeutic device of claim 1, further comprising a perforated inner wound layer disposed below the circuit board, the perforated inner wound layer comprising a plurality of openings and an adhesive periphery for providing a seal between the external layer and the internal layer.

3. The therapeutic device of claim 1, wherein the circuit board comprises an elastomeric thermoplastic film configured to allow for soldering of the processor, the at least one wound monitoring sensor, and the wireless transceiver on traces with soldered connections that can stretch and rebound back to original shape.

4. The therapeutic device of claim 3, wherein soldering is single, double, or multi-sided soldering.

5. The therapeutic device of claim 1, wherein the at least one wound monitoring sensor includes at least one of the following sensors: an acceleration sensor, a chemical sensor, a current sensor, a conductivity sensor, a heart rate sensor, a movement sensor, a genomic sensor, a gaseous sensor, a metabolic sensor, a moisture sensor, an optical sensor, a pressure sensor, a pH sensor, a perfusion sensor, a shear sensor, a temperature sensor, and a voltage sensor; and wherein the device has three-dimensional stretching and deformability with greater than 98% recovery in returning to an original shape after distortion forces are removed.

6. The therapeutic device of claim 1, wherein the at least one wound monitoring sensor is configured to monitor at least one wound characteristic, a metabolic profile, and a genomic signature wherein the at least one of wound characteristic, metabolic profile, and the genomic signature is related to development, deterioration or healing associated with dermal compromise; and wherein the therapeutic device further comprises a perforated inner wound layer positioned below the circuit board.

7. The therapeutic device of claim 1, wherein the at least one sensor is a gaseous sensor, and the gaseous sensor is configured to sense at least one of the following: methane gas, carbon dioxide gas, nitrogen dioxide gas, oxygen gas, and ozone gas.

8. The therapeutic device of claim 1, wherein the at least one sensor is an optical sensor, and the optical sensor is configured to sense at least one of the following: ultraviolet light, visible light, infrared light, and colorimetric light.

9. The therapeutic device of claim 1, wherein the wireless transceiver is configured to communicate wirelessly on industrial, scientific, and medical (ISM) frequency bands.

10. The therapeutic device of claim 9, wherein the processor is configured to receive data from the at least one sensor.

11. The therapeutic device of claim 1, wherein the amount of gas is oxygen.

12. The therapeutic device of claim 1, wherein the amount of gas is at least one of the following: methane, carbon dioxide, nitrogen dioxide, ozone, ambient air, or any combination of the foregoing.

13. A therapeutic device for wound monitoring, said device comprising:

a gaseous reservoir having a periphery that is configured to adhere to a user's skin about a wound on the user's skin, the gaseous reservoir comprising:

an external layer that is impermeable to gas and moisture;

an internal layer having a periphery adhered to the external layer;

a spacer layer disposed between the external layer and the internal layer, the spacer layer creating a space between the external and internal layers;

an amount of gas contained within the space between the external layer and the internal layer;

wherein at least a portion of the internal layer is semipermeable and configured to allow a portion of the amount of gas to diffuse from the gaseous reservoir toward the user's wound;

a bendable, stretchable, film-based circuit board disposed below the internal layer, the circuit board comprising a processor, at least one wound monitoring sensor that detects or measures physical properties at or proximate the wound and communicates data to the processor, and a wireless transceiver; and a perforated inner wound layer disposed below the circuit board, the perforated inner wound layer comprising a plurality of openings configured to allow the at least one sensor to be in communication with the wound.

14. The therapeutic device of claim 13, wherein the circuit board comprises a stretchable elastomeric thermoplastic film that allows for soldering of electronic components on traces with soldered connections that can stretch and rebound back to original shape.

15. The therapeutic device of claim 14, wherein soldering is single, double, or multi-sided soldering.

16. The therapeutic device of claim 13, wherein the at least one wound monitoring sensor includes at least one of the following sensors: an acceleration sensor, a chemical sensor, a current sensor, a conductivity sensor, a heart rate sensor, a movement sensor, a genomic sensor, a gaseous sensor, a metabolic sensor, a moisture sensor, an optical sensor, a pressure sensor, a pH sensor, a perfusion sensor, a shear sensor, a temperature sensor, and a voltage sensor.

17. The therapeutic device of claim 16, wherein the gaseous sensor includes sensing at least one of the following: methane gas, carbon dioxide gas, nitrogen dioxide gas, oxygen gas, and ozone gas.

18. The therapeutic device of claim 16, wherein the optical sensor senses at least one of the following: ultraviolet light, visible light, infrared light, and colorimetric light.

19. The therapeutic device of claim 13, wherein the at least one sensor is configured to monitor at least one wound characteristic, a metabolic profile, and a genomic signature, wherein the at least one wound characteristic, the metabolic profile, and the genomic signature are related to development, deterioration or healing associated with dermal compromise.

20. A therapeutic device for monitoring a wound, said device comprising:

an outer layer that is impermeable to gas and moisture;

an internal layer having a periphery adhered to an underside of the outer layer thereby creating a gaseous reservoir containing an amount of gas between the outer layer and the internal layer;

a spacer layer disposed between the outer layer and the internal layer, the spacer layer having a thickness and configured to absorb fluid and wound exudate from a user's wound, whereby the thickness creates a space between the outer layer and the internal layer;

a bendable, flexible and stretchable, film-based circuit board disposed on the internal layer on a surface away from the outer layer, the circuit board comprising a processor, at least one sensor, and a wireless transceiver; and a perforated inner wound layer coupled to the outer layer, the perforated inner wound layer comprising a plurality of openings and an adhesive periphery for providing a seal between the outer layer and the internal layer, and wherein the perforated inner wound layer further comprises an adhesive wound surface configured to adhere to a user's skin about a wound.

21. The therapeutic device of claim 20, wherein the internal layer is semipermeable to allow a portion of the amount of gas to diffuse from the gaseous reservoir toward the user's wound, and to allow moisture to be absorbed from the user's wound.

22. The therapeutic device of claim 20, wherein the circuit board comprises a stretchable elastomeric thermoplastic film that allows for double-sided soldering of electronic components on traces with soldered connections that can stretch and rebound back to original shape.

23. The therapeutic device of claim 20, wherein the at least one sensor includes at least one of the following digital or analog data sensors: an acceleration sensor, a chemical sensor, a current sensor, a conductivity sensor, a heart rate sensor, a movement sensor, a genomic sensor, a gaseous sensor, a metabolic sensor, a moisture sensor, an optical sensor, a pressure sensor, a pH sensor, a perfusion sensor, a shear sensor, a strain sensor, a temperature sensor, and a voltage sensor.

24. The therapeutic device of claim 23, wherein the gaseous sensor includes sensing at least one of the following: methane gas, carbon dioxide gas, nitrogen dioxide gas, oxygen gas, and ozone gas.

25. The therapeutic device of claim 20, wherein the amount of gas is at least one of the following: methane gas, carbon dioxide gas, nitrogen dioxide, ozone, or ambient air or any combination thereof.

* * * * *